United States Patent
Nakamura et al.

(10) Patent No.: US 10,457,866 B2
(45) Date of Patent: Oct. 29, 2019

(54) DRY ETCHING GAS AND DRY ETCHING METHOD

(71) Applicant: Central Glass Company, Limited, Ube-shi, Yamaguchi (JP)

(72) Inventors: Yosuke Nakamura, Tokyo (JP); Masaki Fujiwara, Tokyo (JP); Hiroyuki Oomori, Ube (JP); Akifumi Yao, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/560,332

(22) PCT Filed: Mar. 4, 2016

(86) PCT No.: PCT/JP2016/056703
§ 371 (c)(1),
(2) Date: Sep. 21, 2017

(87) PCT Pub. No.: WO2016/163184
PCT Pub. Date: Oct. 13, 2016

(65) Prior Publication Data
US 2018/0066187 A1 Mar. 8, 2018

(30) Foreign Application Priority Data
Apr. 6, 2015 (JP) .................. 2015-077775

(51) Int. Cl.
*C07C 17/383* (2006.01)
*C07C 21/18* (2006.01)
(Continued)

(52) U.S. Cl.
CPC ............ *C09K 13/08* (2013.01); *C07C 17/383* (2013.01); *C07C 21/18* (2013.01); *C23F 1/10* (2013.01);
(Continued)

(58) Field of Classification Search
None
See application file for complete search history.

(56) References Cited

U.S. PATENT DOCUMENTS

| 2004/0147698 A1 | 7/2004 | Tanaka et al. |
| 2005/0245774 A1 | 11/2005 | Mukhopadhyay et al. |

(Continued)

FOREIGN PATENT DOCUMENTS

| JP | 2007-302663 A | 11/2007 |
| JP | 2007-535561 A | 12/2007 |
| JP | 2010-180134 A | 8/2010 |
| JP | 2012-114402 A | 6/2012 |

OTHER PUBLICATIONS

International Search Report (PCT/ISA/210) issued in PCT Application No. PCT/JP2016/056703 dated May 17, 2016 (One (1) page).
Japanese-language Written Opinion (PCT/ISA/210) issued in PCT Application No. PCT/JP2016/056703 dated May 17. 2016 (Five (5) pages).

*Primary Examiner* — Stephanie P Duclair
(74) *Attorney, Agent, or Firm* — Crowell & Moring LLP

(57) ABSTRACT

What is disclosed is a dry etching gas containing 1,3,3,3-tetrafluoropropene, wherein 1,3,3,3-tetrafluoropropene has purity of 99.5 mass % or more, and a total of concentration of each mixed metal component of Fe, Ni, Cr, Al, and Mo is 500 mass ppb or less. Furthermore, regarding to the dry etching gas, it is preferable that a content of nitrogen is 0.5 volume % or less, and that a content of water is 0.05 mass % or less. In a dry etching with a plasma gas obtained by making a dry etching gas into plasma, the dry etching gas of the present invention can improve etching selectivity of silicon-based material with respect to a mask.

8 Claims, 1 Drawing Sheet

(51) Int. Cl.
   *C09K 13/08*      (2006.01)
   *C23F 1/10*       (2006.01)
   *C23F 1/12*       (2006.01)
   *H01L 21/306*     (2006.01)
   *H01L 21/3065*    (2006.01)
   *H01L 21/3105*    (2006.01)
   *H01L 21/311*     (2006.01)
   *H01L 21/3213*    (2006.01)

(52) U.S. Cl.
   CPC .............. *C23F 1/12* (2013.01); *H01L 21/306* (2013.01); *H01L 21/3065* (2013.01); *H01L 21/30621* (2013.01); *H01L 21/31055* (2013.01); *H01L 21/31116* (2013.01); *H01L 21/32135* (2013.01)

(56) References Cited

U.S. PATENT DOCUMENTS

| | | | |
|---|---|---|---|
| 2007/0265478 A1 | 11/2007 | Ji et al. | |
| 2008/0203353 A1* | 8/2008 | Ji | G07C 17/208 252/79.1 |
| 2012/0123172 A1* | 5/2012 | Hibino | B01J 21/04 570/160 |
| 2013/0105728 A1* | 5/2013 | Umezaki | H01L 21/31116 252/79.1 |

* cited by examiner

DRY ETCHING GAS AND DRY ETCHING METHOD

TECHNICAL FIELD

The present invention relates to a dry etching gas containing 1,3,3,3-tetrafluoropropene and a dry etching method.

BACKGROUND ART

In recent years, miniaturization in semiconductor manufacturing technology increases a technical difficulty level in processing a contact hole, etc., so high etching selectivity in a layer of processing material such as silicon oxide with respect to a photoresist film has been required. Therefore, technical development has been proceeded by approaches from a lot of aspects such as used material, equipment, and processing method.

From such a situation, as a dry etching gas which is applicable to a state-of-the-art dry etching process, 1,3,3,3-tetrafluoropropene has been developed (Patent Document 1). As compared with carbon tetrafluoride, hexafluoro-1,3-butadiene, and fluorine, which are industrially widely used as an etching gas for a silicon-based material, this compound is capable of etching a silicon-based material with a high aspect ratio and a low side etching ratio with respect to the silicon-based material. Furthermore, this compound is capable of obtaining a good processing shape of a contact hole, so usability of this compound has been recognized. Furthermore, 1,3,3,3-tetrafluoropropene has zero ozone depleting potential and low GWP (global warming potential), so it is a material having low global environmental load as compared with perfluorocarbons and hydrofluorocarbons, which are generally used as an etching agent.

1,3,3,3-tetrafluoropropene has a double bond of carbon-carbon. A part of carbon-carbon bond is dissociated by plasma, and polymerization is proceeded. 1,3,3,3-tetrafluoropropene deposits polymers of fluorocarbon on an etching mask such as a photoresist film during etching. Thereby, etching of the mask is prevented, and etching selectivity between an etching object and the mask can be improved. Therefore, 1,3,3,3-tetrafluoropropene has attracted a lot of attentions as a dry etching gas which is applicable to a state-of-the-art dry etching process.

As a method for manufacturing 1,3,3,3-tetrafluoropropene, a method where 1-chloro-3,3,3-trifluoropropene and hydrogen fluoride are reacted (Patent Document 2); a method where $CF_3X$ and $CXH=CHX$ ("X" is fluorine, chlorine, bromine, or iodine) are reacted (Patent Document 3); etc. are well-known.

PRIOR ART DOCUMENTS

Patent Documents

Patent Document 1: Japanese Patent Application Publication No. 2012-114402 (JP Patent 5,434,970)
Patent Document 2: Japanese Patent Application Publication No. 2010-180134 (JP Patent 5,187,212)
Patent Document 3: Japanese Translation of PCT International Application Publication No. JP-T-2007-535561 (JP Patent 4,864,878)

SUMMARY OF THE INVENTION

However, in case of conducting etching of a semiconductor device while providing 1,3,3,3-tetrafluoropropene charged into a vessel to a dry etching device, there is a case where etching selectivity of a silicon-based material with respect to an etching mask is not sufficient depending on a use. That has been a problem.

It is an object of the present invention to improve etching selectivity of a silicon-based material with respect to an etching mask in a dry etching using 1,3,3,3-tetrafluoropropene.

The present inventors earnestly studied to solve the above problem. Consequently, in case of etching with 1,3,3,3-tetrafluoropropene, if a metal component derived from a manufacturing process, etc. is mixed over a fixed amount as an impurity in. a gas, a double bond of carbon-carbon in excited 1,3,3,3-tetrafluoropropene is dissociated by a metal catalyst effect, and polymer-forming on a mask is prevented. These were found. When the polymer-forming on the mask is prevented, etching of the mask is processed. Therefore, that causes a lowering in etching selectivity with respect to an etching object. Particularly, the present inventors found that substances that lower etching selectivity are metal elements such as Fe, Ni, Cr, Al, and Mo, and the lowering in etching selectivity is caused by using a dry etching gas containing these metal components over a fixed amount with respect to 1,3,3,3-tetrafluoropropene.

Furthermore, the present inventors found that it is needed that a content of the metal component contained in 1,3,3,3-tetrafluoropropene is limited to be less than the fixed amount in order to achieve a dry etching with high selectivity while using refined highly-pure 1,3,3,3-tetrafluoropropene charged in a vessel. Therefore, the present invention has been invented.

That is, the present application provides following inventions described in [Invention 1] to [Invention 12].

[Invention 1]
A dry etching gas containing 1,3,3,3-tetrafluoropropene, wherein 1,3,3,3-tetrafluoropropene has purity of 99.5 mass % or more, and a total of concentration of each mixed metal component of Fe, Ni, Cr, Al, and Mo in 1,3,3,3-tetrafluoropropene is 500 mass ppb or less.

[Invention 2]
The dry etching gas as described in Invention 1, wherein a content of nitrogen is 0.5 volume % or less.

[Invention 3]
The dry etching gas as described in Invention 1 or 2, a content of water is 0.05 mass % or less.

[Invention 4]
The dry etching gas as described in any one of Inventions 1 to 3, wherein the total of concentration of each metal component is 300 mass ppb or less.

[Invention 5]
The dry etching gas as described in any one of Inventions 1 to 4, wherein each metal component is derived from a metal catalyst used in a synthesis reaction of 1,3,3,3-tetrafluoropropene or metal facilities used in manufacturing.

[Invention 6]
The dry etching gas as described in any one of Inventions I to 5, wherein the dry etching gas further contains an additive gas and an inert gas.

[Invention 7]
The dry etching gas as described in Invention 6, wherein the additive gas is an oxidized gas.

[Invention 8]
The dry etching gas as described in any one of Inventions 1 to 7, wherein the dry etching gas selectively etches at least one silicon-based material selected from a group consisting of silicon oxide, silicon nitride, and silicon oxynitride with respect to a mask.

[Invention 9]

A vessel with a valve charged with the dry etching gas described in any one of Inventions 1 to 8.

[Invention 10]

A dry etching method, wherein at least one silicon-based material selected from the group consisting of silicon oxide, silicon nitride, and silicon oxynitride is etched with respect to a mask while using a plasma gas obtained by making the dry etching gas claimed in any one of claims 1 to 8 into plasma.

[Invention 11]

A dry etching method, wherein at least one silicon-based material selected from a group consisting of silicon oxide, silicon nitride, and silicon oxynitride is etched with respect to a mask while using a plasma gas obtained by making a dry etching gas into plasma, the dry etching gas consisting of: 1,3,3,3-tetrafluoropropene wherein 1,3,3,3-tetrafluoropropene has purity of 99.5 mass % or more, and the total of concentration of each mixed metal component of Fe, Ni, Cr, Al, and Mo in 1,3,3,3-tetrafluoropropene is 500 mass ppb or less; an oxidized gas; and an inert gas.

[Invention 12]

The dry etching method as described in Invention 11, a silicon-based material is selectively etched with selectivity with respect to a mask of 10 or more.

Effect of the Invention

According to the present invention, it is possible to improve etching selectivity of a silicon-based material with respect to an etching mask in a dry etching using 1,3,3,3-tetrafluoropropene.

DETAILED DESCRIPTION

<Dry Etching Gas>

Figure 1:
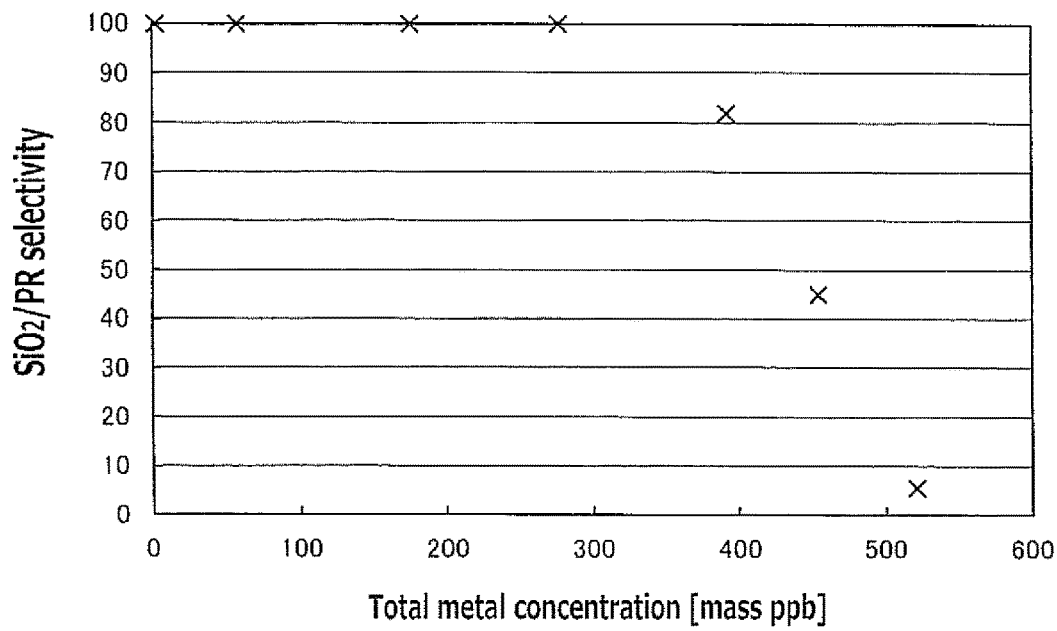
FIG. 1 is a graph obtained by plotting $SiO_2$/PR selectivity in Examples 1 to 6 and Comparative Example 1.

A dry etching gas of the present invention is 1,3,3,3-tetrafluoropropene having purity of 99.5 mass % or more and 1,3,3,3-tetrafluoropropene where a total of concentrations of each mixed metal component of Fe, Ni, Cr, Al, and Mo is 500 mass ppb or less. It is more preferable that the total of concentrations of each metal component is 300 mass ppb or less. 1,3,3,3-tetrafluoropropene used in the present invention has purity of 99.5 mass % or more, more preferably, it has purity of 99.7 mass % or more. The purity is preferable to be higher, but the purity is 99.999 mass % or less in reality because there is an upper limit in purification. Furthermore, the total of concentration of each metal component in 1,3,3,3-tetrafluoropropene used in the present invention is 500 mass ppb or less. The total is preferable to be lower, but the total is 0.1 mass ppb or more in reality. Furthermore, a content of nitrogen is preferable to be 0.5 volume % or less with respect to the total amount of 1,3,3,3-tetrafluoropropene. A content of water is preferable to be 0.05 mass % or less with respect to the total amount of 1,3,3,3-tetrafluoropropene.

The metal components are contained in the gas as particles or clusters of metal or metal compound, or as gaseous body of metal halide or metal complex, which have relatively high vapor pressure.

Fe, Ni, Cr, Al, and Mo are derived from a catalyst used in a manufacturing process, or stainless steel or anticorrosion alloy frequently used in manufacturing facilities. Furthermore, these metals are easy to be contained in 1,3,3,3-tetrafluoropropene, and prevent polymer-forming of 1,3,3,3-tetrafluoropropene.

1,3,3,3-tetrafluoropropene has a double bond of carbon-carbon in its molecule, and has been used as a raw material of fluororesin, etc. When 1,3,3,3-tetrafluoropropene is provided into plasma as an etching gas, at the same time as etching species such as $CF_x^+$ occur, polymerization reaction of a part of 1,3,3,3-tetrafluoropropene proceeds, and it is deposited as polymer on a mask and a side wall. By the deposition film, the mask and the side wall can be protected, and etching with a high aspect ratio and a low side etching ratio is realized. However, the present inventors found that in case of etching with 1,3,3,3-tetrafluoropropene, if the metal component derived from a manufacturing process, etc. is mixed over a fixed amount as impurities in a gas, the double bond of carbon-carbon in excited 1,3,3,3-tetrafluoropropene is dissociated by a metal catalyst effect, and that polymer-forming is prevented. According to the present invention, particularly, contents of metal elements such as Fe, Ni, Cr, Al, and Mo, which are substances that lower etching selectivity, are lowered below a predetermined value, and thereby, deposition of the polymer on the mask is promoted, and etching selectivity between the mask and an etching object can be improved.

In the present invention, the purity of 1,3,3,3-tetrafluoropropene is a value measured by gas chromatography using a flame ionizing type detector (FID) as a detector. Furthermore, the content of the metal component is a value measured by an inductively coupled plasma mass spectrometry (ICP-MS). The content of nitrogen is a value measured by gas chromatography using a thermal conductivity detector (TCD) as a detector. The content of water is a value measured by using a fourier transform infrared spectrophotometer (FT-IR).

As long as 1,3,3,3-tetrafluoropropene used for dry etching has the purity of 99.5 mass % or more and is where the content of the metal component is 500 mass ppb or less, its manufacturing method is particularly limited. Especially, what is obtained through a process of refining crude 1,3,3,3-tetrafluoropropene with a rectifying column having a theoretical plate number of 30 or more is preferable.

<Manufacturing of Crude 1,3,3,3-tetrafluoropropene>

Crude 1,3,3,3-tetrafluoropropene can be manufactured by methods described in the above-mentioned Japanese Patent Application Publication No. 2010-180134 and Japanese Translation of PCT International Application Publication No. JP-T-2007-535561. The former is a method where an unreacted raw material or an intermediate is processed with activated carbon, and it is reused as a raw material again, when 1,3,3,3-tetrafluoropropene is obtained by reacting 1-chloro-3,3,3-trifluoropropene with hydrogen fluoride. On the other hand, the latter is a method where after $CF_3CH=CHX^3$ is obtained by reacting $CF_3X^1$ with $CX^2H=CHX^3$ (X is fluorine, chlorine, bromine, or iodine), 1,3,3,3-tetrafluoropropene is obtained by fluorination. In these manufacturing methods, a metal catalyst such as chromium-supporting activated carbon is used. Therefore, a metal component derived from the metal catalyst is sometimes mixed in obtained 1,3,3,3-tetrafluoropropene. Furthermore, a metal component derived from metal facilities having been used in manufacturing is sometimes mixed in obtained 1,3,3,3-tetrafluoropropene.

\<Refining of Crude 1,3,3,3-tetrafluoropropene\>

Obtained crude 1,3,3,3-tetrafluoropropene is purified by distillation, and thereby the purity of 1,3,3,3-tetrafluoropropene can be improved. In particular, a rectifying column having a high theoretical plate number is preferably used in order to efficiently remove the mixed metal component. The theoretical plate number of used rectifying column is generally 20 plates or more, preferably 30 plates or more. In terms of manufacturing, it is preferable that the upper limit of the theoretical plate number is 100 plates.

A pressure in rectification is generally ordinary pressure to 5 atom as gauge pressure, preferably ordinary pressure to about 2 atom. Regarding to a ratio between reflux quantity and extracting quantity (hereinafter, it may be referred to as "reflux ratio"), in order to remove a minute amount of the metal component contained in 1,3,3,3-tetrafluoropropene, it is preferable that the reflux ratio is set to be 40:1 or more. If the reflux ratio is too small, the metal component is not efficiently removed, so improvement of the purity of 1,3,3,3-tetrafuluoropropene is small. Furthermore, initial distillate is increased, so a quantity of 1,3,3,3-tetrafuluoropropene, which is substantially gathered as a product, is decreased. Furthermore, if the reflux ratio is excessively too large, a lot of times are spent on a collection at one extracting, so a lot of times are required in rectification itself.

As a system of rectification, in case that a production amount is small, a batchwise system can be used. However, in case that the production amount is large, a continuous system where several rectifying columns are used can be adopted. Furthermore, rectification can be done by combining an extractive distillation operation with an extraction solvent added therein.

Furthermore, in case of refining crude 1,3,3,3-tetrafuluoropropene while using a rectifying column, rectification can be done in an inert gas. The inert gas is not particularly limited. For example, it is possible to cite helium, neon, argon, krypton, xenon, etc., which belong to group 18 in the periodic table. In terms of easiness to obtain on an industrial scale, helium and argon are preferable.

A metal component which is mixed at a small amount in a manufacturing process and is derived from a catalyst and facilities is not always removed sufficiently in even 1,3,3,3-tetrafuluoropropene whose purity is increased to 99.5 mass % or more by the above purification method. In case of using 1,3,3,3-tetrafuluoropropene containing the metal element at a prescribed amount or more as the dry etching gas, selectivity between the mask and the etching object is lowered.

Furthermore, as to nitrogen contained in 1,3,3,3-tetrafuluoropropene, the content of nitrogen can be a problem. If the content of nitrogen is large or if there are variations in the content for each vessel, extreme fluctuation of an etching rate in a dry etching, that is, nonuniformity of the etching rate in each batch is caused. Therefore, there is a risk of causing destabilization of the manufacturing process. Accordingly, the state where the nitrogen contained in 1,3,3,3-tetrafuluoropropene has been reduced as much as possible is preferable.

There is no particular limitation in a method for removing nitrogen contained in 1,3,3,3-tetrafluoropropene. For example, it is possible to cite a method where rectification is conducted in an inert gas of group 18 in case that the above metal component is removed by rectification; and a method where an operation of extracting fraction is conducted after subjecting 1,3,3,3-tetrafuluoropropene to a simple distillation. In case of the latter, as nitrogen is extracted together with 1,3,3,3-tetrafuluoropropene by the simple distillation, the content of nitrogen remaining in a vessel and contained in 1,3,3,3-tetrafuluoropropene is reduced. Extracted 1,3,3,3-tetrafuluoropropene is stored, and by adding it into next batch, retrieving and reuse can be done.

Furthermore, there is no particular limitation in a method for removing water contained in 1,3,3,3-tetrafluoropropene, and a general method such as a method where it is brought into contact with an absorbent can be adopted.

As the absorbent, it is possible to use molecular sieves, alumina, etc. As many kinds of molecular sieves and alumina are commercially available, it is possible to properly select from among them. Especially, molecular sieves 3A, 4A, 5A, etc. are preferable, and 3A is particularly preferable. Furthermore, as alumina, activated alumina which is generated by thermal dehydration of hydrated alumina and which has low crystallinity is preferable. It is desirable that the absorbents such as molecular sieves and alumina are activated by a burning operation, etc. before 1,3,3,3-tetrafuluoropropene is brought into contact with the absorbents. The absorbents can absorb much water by being activated in advance. In this way, it is possible to reduce a water amount contained in 1,3,3,3-tetrafuluoropropene to 0.05 mass % or less by bringing 1,3,3,3-tetrafuluoropropene into contact with the absorbent. If the water amount is large, water remains adsorbed on the processed surface after etching processing of a substrate. Thereby, there are risks of separating a laminated film in a wiring forming step of copper, etc. and causing corrosion of an embedded wire. Therefore, it is preferable that the water amount is reduced as much as possible.

As explained above, high-purity 1,3,3,3-tetrafluoropropene can be obtained by conducting a rectifying step of rectifying crude 1,3,3,3-tetrafluoropropene in a crude reaction product to be 99.5 mass % or more in purity and to be 500 mass ppb or less in the content of the metal component; and a step of removing water by bringing 1,3,3,3-tetrafuluoropropene into contact with the absorbent.

The high-purity 1,3,3,3-tetrafuluoropropene can be charged in a vessel with a valve. This charging vessel is not particularly limited in its material as long as it is a metal pressure vessel. Generally, manganese steel, chromium molybdenum steel, stainless steel, nickel steel, and aluminum alloy steel are used therein. As to the valve (hereinafter, it may be referred to as "vessel valve"), considering corrosion, safety, etc. of the compound, it is desirable to use a vessel valve which is based on High Pressure Gas Safety Act and JIS-B8246. As this vessel valve, it is possible to cite diaphragm type, key plate type, direct diaphragm seal type, etc. In terms of easiness to obtain, a manganese steel vessel with a diaphragm type valve is desirable.

\<Use as a Gas for Plasma Reaction Dry Etching\>

A silicon-based material can be selectively etched by conducting plasma reaction dry etching while using high-purity 1,3,3,3-tetrafuluoropropene where the content of metal components is reduced.

As a silicon-based material which is an etching object, it is possible to cite silicon oxide, silicon nitride, and silicon oxynitride. As a silicon oxide, $SiO_2$ can be cited. As a silicon nitride, $Si_3N_4$ can be cited. Silicon oxynitride is represented by $Si_xO_yN_z$, and $Si_4O_5N_3$, etc. can be cited. Silicon oxynitride can be obtained by introducing nitrogen into silicon oxide with nitrogen plasma. When etching these silicon-based materials, selectively with respect to a mask is preferable to be 10 or more, more preferable to be 30 or more, and particularly preferable to be 100 or more.

As a mask provided on the silicon-based material in the dry etching, a photoresist film or an amorphous carbon film can be used. Particularly, it is preferable to use the photoresist film which is capable of easily forming pattern formation.

In case of using high-purity 1,3,3,3-tetrafuluoropropene in the plasma reaction dry etching, it is preferable to use not only 1,3,3,3-tetrafluoropropene but also together with an additive gas and an inert gas. In order to increase the etching rate to improve productivity, it is preferable that an oxidized gas is added as the additive gas. Concretely, it is possible to cite oxygen-containing gas such as $O_2$, $O_3$, CO, $CO_2$, $COCl_2$, $COF_2$, and $NO_2$ and halogen-containing gas such as $F_2$, $NF_3$, $Cl_2$, $Br_2$, $I_2$, and $YF_n$ (Y=Cl, Br, or I, $1 \leq n \leq 7$). Especially, as being capable of further increasing the etching rate to metal, $O_2$, $COF_2$, $F_2$, $NF_3$, and $Cl_2$ are preferable, and $O_2$, is particularly preferable.

Furthermore, when to reduce an amount of F radical promoting isotropic etching is desired, to add a reducing gas is effective. As the reducing gas, it is possible to cite $CH_4$, $C_2H_2$, $C_2H_4$, $C_2H_6$, $C_3H_4$, $C_3H_6$, $C_3H_8$, HF, HI, HBr, HCl, NO, $NH_3$, and $H_2$.

Furthermore, as an inert gas, it is possible to use $N_2$, He, Ar, Ne, Kr, etc.

Regarding to each proportion in case of simultaneously using 1,3,3,3-tetrafuluoropropene, additive gas, and inert gas, it is preferable that the propene:additive gas:inert gas=1 to 45 volume %:1 to 50 volume %:5 to 98 volume %.

Furthermore, in case of mixing the additive gas and the inert gas into the dry etching gas, it is preferable to use a high-purity additive gas and a high-purity inert gas so as not to mix metal component derived from the additive gas and the inert gas. Therefore, metallic impurity in plasma is almost derived from 1,3,3,3-tetrafluoropropene, and a ratio of 1,3,3,3-tetrafluoropropene to the metallic impurity in plasma is almost equal to the content of metal component of 1,3,3,3-tetrafluoropropene provided to plasma.

As a dry etching method, various etching methods such as reactive ion etching (RIE), electron cyclotron resonance (ECR) plasma etching, microwave etching, etc. can be used, and reaction conditions are not particularly limited therein. An etching method used in the present invention is a method where plasma of propene being an object is generated in an etching treatment device, and a prescribed part of a workpiece in the device is etched by the plasma. For example, in manufacturing of a semiconductor, silicon oxide film, silicon nitride film, or silicon oxynitride film is formed on a wafer, a resist provided with a particular opening part is applied on an upper part, and the silicon oxide film, etc. are removed by providing a dry etching agent from the resist opening part. Thereby, a prescribed pattern is formed on the silicon oxide film, etc.

Regarding to a plasma generating device used when conducting etching, it is not particularly limited. However, for example, devices in high frequency induction system, microwave system, etc. are preferable to be used.

Regarding to a pressure in conducting etching, in order to effectively conduct the etching, a gas pressure is preferable to be a range of 0.133 Pa to 133 Pa. If the pressure is lower than 0.133 Pa, the etching rate is slow. On the other hand, if the pressure exceeds 133 Pa, resist selectivity is sometimes impaired.

Furthermore, a flow rate of a used gas depends on a size of an etching device, so a skilled person can properly adjust the flow rate while depending on a used device.

Furthermore, a temperature in conducting the etching is preferable to be 300° C. or less. Especially, in order to conduct high selective etching, it is preferable to be 240° C. or less. In case of high temperature exceeding 300° C., a resist is remarkably etched, so that is not preferable.

Although reaction time of etching treatment is not particularly limited, it is about 5 to 30 minutes. However, because of depending on a course after the etching treatment, a skilled person can properly adjust the reaction time while observing an etching state.

EXAMPLES

Hereinafter, the present invention is further explained in details with examples. However, the present invention is not limited in a range of the invention by the following examples.

The purity of 1,3,3,3-tetrafluoropropene was measured by gas chromatography using a flame ionizing type detector (FID) as a detector. Furthermore, the content of metal component was measured by an inductively coupled plasma mass spectrometry (ICP-MS).

The content of nitrogen was measured by gas chromatography using a thermal conductivity detector (TCD) as a detector. The content of water was measured by using a fourier transform infrared spectrophotometer (FT-IR).

[Manufacturing Example]
(Manufacturing of Crude 1,3,3,3-tetrafluoropropene)

100 g of granular coconut shell charcoal (granular SHIRASAGI G2X, 4-6 mesh, manufactured by Japan Enviro-Chemicals, Limited) and a solution prepared by dissolving 60 g of $Cr(NO_3)_2 \cdot 9H_2O$ (special grade chemical) in 100 g of pure water were mixed and stirred. After left to stand through one day and night, activated carbon was extracted therefrom by filtration. The activated carbon was maintained at 200° C. in an electric furnace and burned for two hours. Thereby, chromium-supporting activated carbon was obtained. The obtained chromium-supporting activated carbon was charged in a cylindrical reaction pipe which is formed of stainless steel (SUS316L). A temperature in the reaction pipe was raised to 200° C. while pouring nitrogen gas at a flow rate of 500 ml/min, and it had been heated until an outflow of water was not observed. Thereby, a gas phase fluorination catalyst was prepared.

150 ml of the gas phase fluorination catalyst was charged in a gas phase reaction device equipped with a cylindrical reaction pipe (formed of stainless steel (SUS316L), inner diameter 27.2 mm, length 30 cm) provided with an electric furnace. A temperature in the reaction pipe was raised to 200° C. while pouring nitrogen gas at a flow rate of about 10 ml/min, and hydrogen fluoride was introduced thereto at a velocity of about 0.10 g/min. Next, the temperature in the reaction pipe was raised to 350° C., to pour the nitrogen gas was stopped, the providing velocity of hydrogen fluoride was set to be 0.73 g/min, 1-chloro-3,3,3-trifluoropropene was vaporized in advance and to provide it into the reaction pipe at a velocity of 0.48 g/min was started. Acidic component was removed by blowing a reactive generated gas flowing out of the reaction pipe into water. A gas where acidic component had been removed was dehydrated by passing it through a calcium chloride column, and introduced to a distillation column which is formed of glasses (five distillation plates). Thereby, continuous distillation was conducted at the same time of reaction. The distillation was conducted by using a column with a vacuum jacket and a fractionator with a vacuum jacket under the conditions of ordinary pressure, condenser temperature of −40° C., and bottom temperature of 10 to 15° C., and a bottom liquid was continuously extracted by a pomp. In a distillate from a column top, gas chromatography purity of 1,3,3,3-tetrafluoropropene was 99.3 mass %.

[Preparation of Sample 1]

220 g of crude 1,3,3,3-tetrafuluoropropene manufactured in the manufacturing example was put into a tank formed of SUS 316 having a capacity of 20 liter. 200 cm$^3$ of molecular sieves 3A (manufactured by UNION SHOWA) was charged in a tube formed of SUS 316 (having a diameter 1 inch× length 60 cm), and 1,3,3,3-tetrafuluoropropene put into the SUS tank was provided therein by a pump. Thereby, water was removed therefrom. 1,3,3,3-tetrafuluoropropene going out from an outlet of the SUS tube was returned to the tank formed of SUS316 and circulated. After five hours, about 5 g of 1,3,3,3-tetrafuluoropropene in the tank formed of SUS316 was sampled to a small-sized cylinder. As a result of water analysis by FT-IR, a water amount of sampled 1,3,3,3-tetrafuluoropropene was 0.03 mass %.

Next, 1,3,3,3-tetrafluoropropene after removing water was put into a vessel having a capacity of 50 liter in a rectifying column formed of SUS316 with a column having theoretical plate number of 30 plates (filler, product name: Sulzer packing), and the vessel was set to be in 10 to 15° C. A temperature in the condenser was set to be about −40° C. Furthermore, total reflux for about 12 hours was conducted to stabilize the inside system. When a temperature in the top column part of the rectifying column got −40° C., to extract fraction at 40:1 of reflux ratio was started to a receiver. Thereby, 180 g of refined 1,3,3,3-tetrafluoropropene was obtained. 160 g of 1,3,3,3-tetrafluoropropene in the receiver was charged into a cylinder formed of manganese steel with a diaphragm type valve having a capacity of 3.4 liter (inside surface roughness: 1S). This charged 1,3,3,3-tetrafluoropropene was regarded as sample 1. An analysis line was connected to a cylinder where the sample 1 was charged, and purity of 1,3,3,3-tetrafluoropropene, a content of metal component, and concentrations of nitrogen and water were measured. As these results, the purity of 1,3,3,3-tetrafluoropropene was 99.7 mass %, the content of metal component was 57 mass ppb (total amount), the concentration of nitrogen was 0.3 volume %, and the concentration of water was 0.03 mass %. The content of metal component was measured by ICP-MS.

[Preparation of Samples 2 to 8]

Samples 2 to 8 of 1,3,3,3-tetrafluoropropene charged in cylinders were obtained by the same preparation way of sample 1 except for modifying the reflux ratio and the number of distillation in rectification conditions. Analysis lines were connected to cylinders where the sample 2 to 8 were charged, and purity of 1,3,3,3-tetrafluoropropene, a content of metal component, and concentrations of nitrogen and water were measured respectively.

[Evaluation Method]

(i) Dry Etching Evaluation of 1,3,3,3-tetrafluoropropene

While using a dry etching device which is CCP (capacity coupling plasma) type using 13.56 MHz of high frequency power supply, etching evaluation of 1,3,3,3-tetrafluoropropene charged in the cylinder was conducted.

A silicon wafer (1 cm square) where a photoresist was applied in thickness of 100 nm as a mask on a silicon oxide film having a film thickness of 200 nm, and where a hole pattern of diameter 60 nm was formed; and a silicon wafer (1 cm square) where a photoresist was applied in thickness of 100 nm as a mask on a silicon nitride film having a film thickness of 200 nm, and where a hole pattern of diameter 60 nm was formed were set in a chamber of an etching device. After an inside system was evacuated, argon gas, 1,3,3,3-tetrafluoropropene, and oxygen gas were introduced at each flow rate of 80 sccm, 10 sccm, and 10 sccm. Furthermore, the gas was flowed while maintaining a pressure at 1 Pa, and dry etching was conducted for two minutes. Furthermore, as ultra-high purity products were used in argon gas and oxygen gas, in each gas, the total concentration of Fe, Ni, Cr, Al, and Mo was 1 mass ppb or less.

Each etching rate was evaluated from film thicknesses of the silicon oxide film or the silicon nitride film and the photoresist after etching, and each etching selectivity was evaluated. In case that the photoresist has been little or no etched, the evaluation of etching selectivity has gotten high, so it has been shown as >100. The dry etching evaluations have been conducted as Examples 1 to 6 and Comparative Examples 1 and 2 while using the samples 1 to 8 charged in the cylinders. The results have been shown in Tables.

TABLE 1

| | Gas purity [mass %] | Metal concentration [mass ppb] | | | | | | Nitrogen concentration [volume %] | Water amount [mass %] |
|---|---|---|---|---|---|---|---|---|---|
| | | Fe | Ni | Cr | Al | Mo | Total concentration | | |
| Sample 1 | 99.7 | 17 | 12 | 9 | 11 | 8 | 57 | 0.3 | 0.03 |
| Sample 2 | 99.7 | 53 | 40 | 29 | 32 | 22 | 176 | 0.3 | 0.03 |
| Sample 3 | 99.7 | 82 | 71 | 45 | 49 | 30 | 277 | 0.3 | 0.03 |
| Sample 4 | 99.7 | 120 | 106 | 63 | 65 | 38 | 392 | 0.3 | 0.03 |
| Sample 5 | 99.7 | 140 | 119 | 75 | 77 | 43 | 454 | 0.3 | 0.03 |
| Sample 6 | 99.7 | 0.7 | 0.6 | 0.3 | 0.2 | 0.2 | 2 | 0.3 | 0.03 |
| Sample 7 | 99.7 | 152 | 133 | 91 | 95 | 50 | 521 | 0.3 | 0.03 |
| Sample 8 | 99.5 | 148 | 135 | 90 | 93 | 49 | 515 | 0.6 | 0.07 |

TABLE 2

| | | Gas purity [mass %] | Total metal concentration [mass ppb] | SiO$_2$/PR selectivity | SiN/PR selectivity |
|---|---|---|---|---|---|
| Ex. 1 | Sample 1 | 99.7 | 57 | >100 | >100 |
| Ex. 2 | Sample 2 | 99.7 | 176 | >100 | >100 |
| Ex. 3 | Sample 3 | 99.7 | 277 | >100 | >100 |
| Ex. 4 | Sample 4 | 99.7 | 392 | 82 | 94 |
| Ex. 5 | Sample 5 | 99.7 | 454 | 45 | 62 |
| Ex. 6 | Sample 6 | 99.7 | 2 | >100 | >100 |
| Com. Ex. 1 | Sample 7 | 99.7 | 521 | 5.6 | 8.6 |
| Com. Ex. 2 | Sample 8 | 99.5 | 515 | 4.2 | 6.5 |

Figure 2:
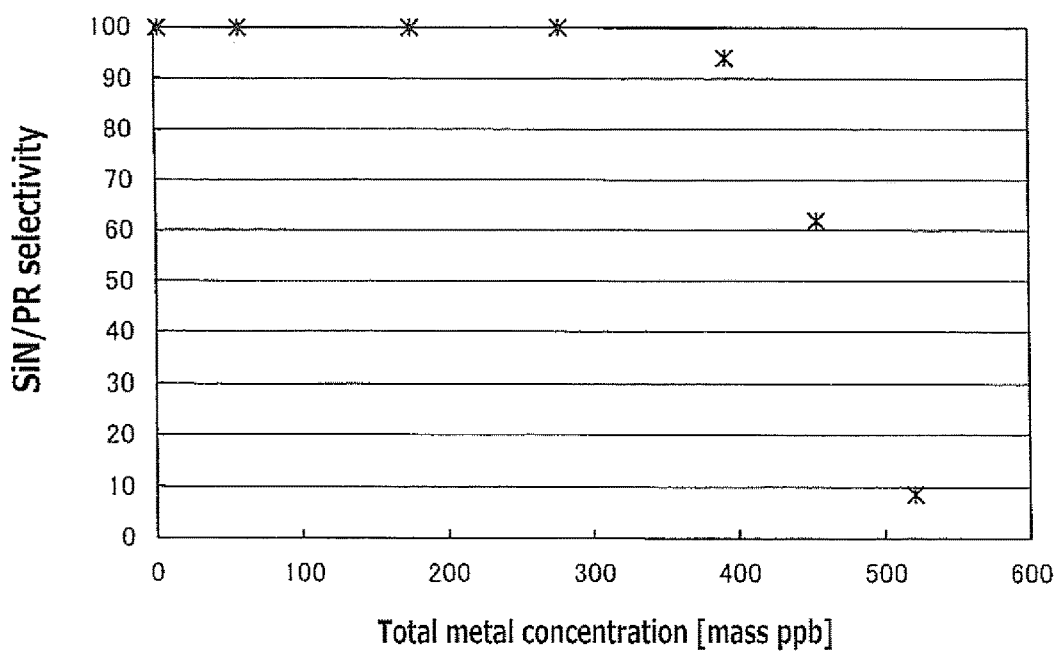
FIG. 2 is a graph obtained by plotting SiN/PR selectivity in Examples 1 to 6 and Comparative Example 1.

FIG. 1 and FIG. 2 are graphs plotting results of Examples 1 to 6 and Comparative Example 1 which are described in Table 2. The total metal concentrations are shown in the horizontal axis. SiO$_2$/PR selectivity or SiN/PR selectivity is shown in the vertical axis. According to FIG. 1 and FIG. 2, it is found that in case that the total concentration of the metal component in 1,3,3,3-tetrafuluoropropene is lower than 500 mass ppb, selectivity between the photoresist (PR) and the silicon oxide film or the silicon nitride film is high, and selective etching has been achieved. Especially, in Examples 1 to 3 and 6 in which the total concentration of the metal component is 300 mass ppb or less, the selectivity exceeds 100, and they have shown particularly high selectivity. On the other hand, in Comparative Examples 1 and 2 in which the total concentration of the metal component is higher than 500 mass ppb, selectivity between the photoresist (PR) and the silicon oxide film or the silicon nitride film has been low as compared with Examples 1 to 6. Especially, in Comparative Example 2 in which the nitrogen concentration and the water amount are large, the selectivity has been lower than that of Comparative Example 1.

INDUSTRIAL APPLICABILITY

A dry etching gas containing 1,3,3,3-tetrafluoropropene of the present invention, which is highly purified, is suitable for a dry etching using a plasma reaction in a semiconductor device manufacturing field.

The invention claimed is:

1. A dry etching gas containing 1,3,3,3-tetrafluoropropene,
   wherein the 1,3,3,3-tetrafluoropropene has a purity of 99.7 mass % or more, a nitrogen content of 0.3 volume % or less and a water content of 0.03 mass % or less, and
   wherein the total of concentrations of Fe, Ni, Cr, Al, and Mo in the 1,3,3,3-tetrafluoropropene is 500 mass ppb or less.

2. The dry etching gas as claimed in claim 1, wherein each metal component is derived from a metal catalyst used in a synthesis reaction of 1,3,3,3-tetrafluoropropene or metal facilities used in manufacturing.

3. The dry etching gas as claimed in claim 1, wherein the dry etching gas further contains an additive gas and an inert gas.

4. The dry etching gas as claimed in claim 3, wherein the additive gas is an oxidized gas.

5. The dry etching gas as claimed in claim 1, wherein the dry etching gas selectively etches at least one silicon-based material selected from a group consisting of silicon oxide, silicon nitride, and silicon oxynitride with respect to a photoresist.

6. A vessel with a valve charged with the dry etching gas claimed in claim 1.

7. A dry etching method, wherein at least one silicon-based material selected from the group consisting of silicon oxide, silicon nitride, and silicon oxynitride is etched with respect to a photoresist while using a plasma gas obtained by making the dry etching gas claimed in claim 1 into plasma.

8. A dry etching method, wherein at least one silicon-based material selected from a group consisting of silicon oxide, silicon nitride, and silicon oxynitride is etched with respect to a photoresist while using a plasma gas obtained by making a dry etching gas into plasma,
   wherein the dry etching gas consists of: 1,3,3,3-tetrafluoropropene, an oxidized gas; and an inert gas,
   wherein the 1,3,3,3-tetrafluoropropene has a purity of 99.7 mass % or more, a nitrogen content of 0.3 volume % or less and a water content of 0.03 mass % or less,
   wherein the total of concentrations of Fe, Ni, Cr, Al, and Mo in the 1,3,3,3-tetrafluoropropene is 500 mass ppb or less, and
   wherein the silicon-based material is selectively etched with selectivity of 100 or more with respect to the photoresist.

* * * * *